United States Patent [19]
Schwartz

[11] Patent Number: 6,117,080
[45] Date of Patent: Sep. 12, 2000

[54] ULTRASONIC IMAGING APPARATUS AND METHOD FOR BREAST CANCER DIAGNOSIS WITH THE USE OF VOLUME RENDERING

[75] Inventor: Gary Allen Schwartz, Seattle, Wash.

[73] Assignee: ATL Ultrasound, Bothell, Wash.

[21] Appl. No.: 08/867,038

[22] Filed: Jun. 4, 1997

[51] Int. Cl.[7] ................................................ A61B 8/00
[52] U.S. Cl. ............................................................. 600/443
[58] Field of Search ..................... 128/916, 915; 600/443, 447, 438

[56] References Cited

U.S. PATENT DOCUMENTS

| 4,043,181 | 8/1977 | Nigam . | |
|---|---|---|---|
| 4,186,747 | 2/1980 | Iinuma . | |
| 4,662,380 | 5/1987 | Riley . | |
| 5,003,979 | 4/1991 | Merickel et al. | 128/915 |
| 5,007,428 | 4/1991 | Watmough | 128/915 |
| 5,315,512 | 5/1994 | Roth | 364/413.25 |
| 5,329,929 | 7/1994 | Sato et al. . | |
| 5,413,106 | 5/1995 | Fujita et al. | 128/916 |
| 5,474,073 | 12/1995 | Schwartz et al. . | |
| 5,485,842 | 1/1996 | Quistgaard | 128/66.07 |
| 5,501,221 | 3/1996 | Foster et al. . | |
| 5,529,070 | 6/1996 | Augustine et al. . | |
| 5,568,811 | 10/1996 | Olstad | 600/443 |
| 5,645,066 | 7/1997 | Gandini et al. | 128/916 |
| 5,706,816 | 1/1998 | Mochizuki et al. | 600/443 |
| 5,709,206 | 1/1998 | Teboul | 128/916 |
| 5,766,129 | 6/1998 | Mochizuki | 600/443 |

OTHER PUBLICATIONS

"Volume Rendering" by Robert A. Drebin et al., *Computer Graphics*, vol. 22, No. 4, Aug. 1988 at pp. 51–58.

Primary Examiner—William E. Kamm
Assistant Examiner—Maulin Patel
Attorney, Agent, or Firm—W. Brinton Yorks, Jr.

[57] ABSTRACT

An ultrasonic diagnostic imaging system is described which produces ultrasonic breast images by acquiring ultrasonic data from a volumetric region of the breast, then volume rendering the data to produce a projection image from the data set. The diagnostic image reveals diagnostic information of the complete volume of breast tissue in a single ultrasonic image.

10 Claims, 5 Drawing Sheets

ULTRASONIC IMAGING APPARATUS AND METHOD FOR BREAST CANCER DIAGNOSIS WITH THE USE OF VOLUME RENDERING

This invention relates to ultrasonic diagnostic imaging systems and, in particular, to the use of ultrasonic imaging systems for breast cancer diagnosis.

Breast cancer is an important concern for women's health. Like most cancers, reduction in breast cancer mortality is promoted by early detection and treatment. It is for this reason that self examination and examination during regular physical examinations are strongly encouraged. The standard breast examination today is a mammogram, in which the breast is compressed and x-rays are transmitted through the breast tissue to expose an x-ray negative. The x-rays which pass through healthy tissue are moderately absorbed by the moderate density of the tissue, which causes healthy tissue to leave a gray shadow image on the x-ray. X-rays which pass through dense particles such as calcifications undergo significant absorption, and the consequent deposit of relatively few photons on the x-ray film will leave a bright spot on the x-ray. X-rays which pass through very soft structures such as cysts are only slightly absorbed, and will leave a relatively dark spot on the x-ray. The radiologist is looking for such bright and dark spots on the mammogram when the diagnosis of the x-ray is performed.

Because the x-rays of the mammogram pass completely through the breast before reaching the film, each x-ray which strikes the film has been affected by every cell in its path of passage through the breast. This means that the mammogram conveys information about the entire organ, since the x-rays forming the mammogram have passed through the complete breast and in the aggregate are functionally related to every cell in the breast. The transmission image thus formed is a projection of all of the tissue of the breast onto a single sheet of film. Mammograms are advantageous for this ability to capture a full summary of the entire breast in a single image.

Ultrasonic imaging is also useful in detecting breast disease. In 1996, Advanced Technology Laboratories, Inc. became the first ultrasound company to receive approval for use of its ultrasound systems in conjunction with mammography or self-examination in the diagnosis of breast lesions. Standard two dimensional ultrasound imaging has proven capable of detecting calcified lesions in the breast on the order of those detectable by mammography. This has largely been due to the improvements in spatial and contrast resolution seen in the beamformers of the ATL ultrasound systems and frequency compounding to reduce speckle noise, coupled with the high frequency, wide bandwidth and large apertures of the ATL L10-5 probe. Recent studies have shown that significant disease is missed with mammography, particularly in dense breast tissue and is detectable with ultrasound. Mammography, however retains a significant advantage in screening applications due to a lesser dependence on operator technique and a more efficient presentation of the image of the entire organ in a single image. Ultrasonic breast examination is an inherently tomographic procedure which requires a tedious, and possibly incomplete scan of many dozen images to see the entire breast. A complete examination requires a review of these dozens of images, and recordkeeping correspondingly requires the maintenance of many ultrasound images. Accordingly, it would be desirable to provide an ultrasonic breast examination which is as convenient to perform, diagnose, and record as a mammographic examination.

In accordance with the principles of the present invention, an apparatus and method are provided for ultrasonic breast examination. In accordance with the inventive technique, the entire breast volume is ultrasonically scanned to acquire a three dimensional data set of the breast. The data set is then volume rendered to form an image of the entire organ. In a preferred embodiment, the volume rendering produces a projection image, thereby capturing a record of the full breast volume in a single image. In accordance with one aspect of the present invention, the breast image data is processed with an inverse intensity-opacity function to more clearly reveal hypoechoic lesions such as cysts. The breast image data is processed with a more conventional, increasing function to reveal dense substances such as microcalcifications. In accordance with another aspect of the present invention, a flow data set of the breast volume is used to mask signals from the hypoechoic lumens of blood vessels when diagnosing hypoechoic lesions. The inventive technique is useful in other applications where hypoechoic bodies are being imaged, such as the bile duct.

Figure 1:
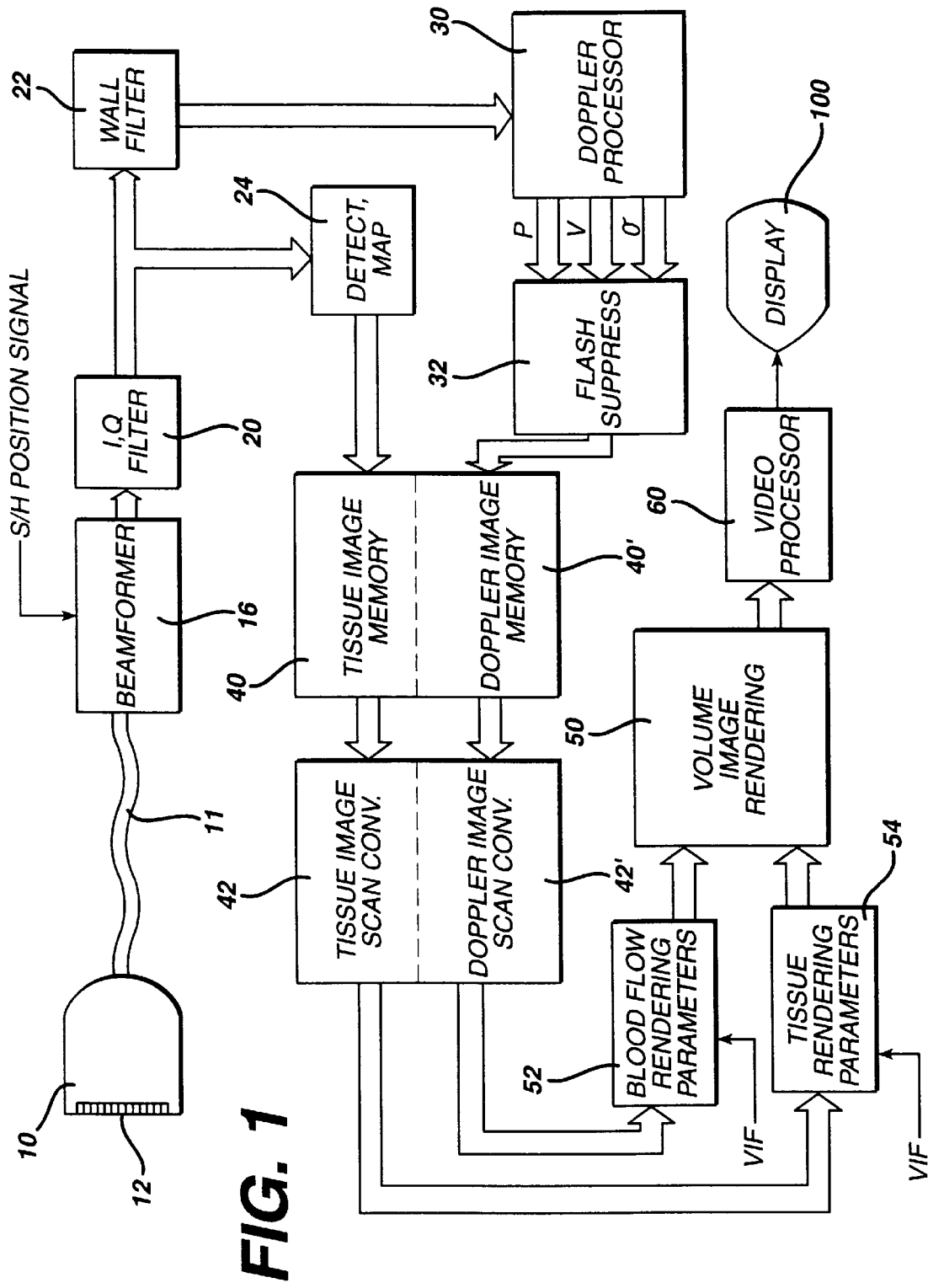
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A scanhead 10 includes a transducer array 12 which transmits ultrasonic pulses into the body of a patient and receives back ultrasonic echoes. The transducer array 12 is pulsed under the control of and echoes are received by a beamformer 16. Ultrasonic beams transmitted and received by the transducer array are steered and focused under control of the beamformer 16, which processes echo signals from a plurality of elements to form scanlines of coherent echo signals. The received echo signals are quadrature detected and filtered by an I,Q filter 20, then processed for either B mode or Doppler display.

For B mode processing the I and Q samples are coupled to a detector and grayscale mapping circuit 24, which produces grayscale signals with brightness corresponding to the intensity of received echo signals. The grayscale signals are stored in a tissue image memory 40 together with information bearing their spatial relationship to the image field. In a preferred embodiment scanlines of grayscale signals are acquired to form a full planar image, and a sequence of B mode planar tissue images is stored in tissue image memory 40. The image planes retain their spatial orientation to each other by being stored in the time or spatial sequence in which they were acquired.

For Doppler processing the I and Q samples undergo highpass filtering in a wall filter 22, then are assembled in ensembles of Doppler data in a Doppler processor 30. The data ensembles are processed by a Doppler technique such as autocorrelation or Fourier transform processing to produce Doppler signals of parameters such as Doppler power (P), velocity (v), or variance (σ). The Doppler signals are processed to remove motion artifacts in a flash suppresser 32, then stored in a Doppler image memory 40' together with information bearing the spatial relationship of the Doppler signals to the image field. In a preferred embodiment scanlines of Doppler signals are acquired to form a full planar image, and a sequence of Doppler images is stored in Doppler image memory 40'. The Doppler images retain their spatial orientation to each other by being stored in the time or spatial sequence in which they were acquired. The tissue and Doppler image information may then, if desired, be scan converted into the desired image format, such as a sector format, in a scan converter 42. Separate scan converters 42,42' may be employed to rapidly scan convert tissue and Doppler images simultaneously, or a single scan converter may be used by time multiplexing the processing of the two types of image information. Scan conversion may also be merged into the rendering operations, whereby the two functions are carried out together (i.e., convert polar coordinate scanlines directly into a rectilinearly addressed three dimensional image.)

In Accordance with the principles of the present invention, the greyscale signal data, the Doppler signal data, or both undergo volume rendering in a volume image rendering processor 50. The rendering process may be performed in accordance with rendering parameters stored in rendering parameter storage areas 52 and 54. As described in U.S. patent [application Ser. No. 08/638,710], these parameters control the manner in which each type of image information will be processed in the rendering. For instance, the user may enter values for the opacity and contrast to be imparted to each type of image information. In a preferred embodiment for breast imaging, discussed below, predetermined intensity-opacity transfer functions are implemented by the parameters to emphasize breast pathology with certain acoustic characteristics which are of interest to the diagnosing physician.

The spatially acquired tissue and/or blood flow image information is volume rendered together to form an image which incorporates all or selected portions of the volumetric region which was scanned. Volume rendering is described in Kaufman, A., *Introduction to Volume Visualizationz, IEEE Computer Society Press.* 1991 at pp 1–18. A preferred technique of volume rendering is a projection image, in which the volumetric signal information is projected into a single diagnostic image, or a set of images which provides multiple viewing angles of the volumetric region, as described in U.S. Pat. Nos. 5,474,073 and 5,485,842. A preferred projection image is produced by a maximum intensity projection process. To produce a maximum intensity image, diagnostic image pixels $P_{x,y}(\theta)$ are formed by analyzing elements of the volumetric data along projection lines intersecting a plane of the data set at an angle θ. For example, suppose that the data set comprises a sequence of N parallel image planes, each having data point in the x,y dimensions in the image plane, and each image plane comprising a z dimension. Suppose that projection lines are symbolically drawn through the image planes normal (θ=90°) to the plane of the first image in the sequence. Each symbolic projection line will intersect pixels $P_z$ as it passes through the image plane data. The pixels along each symbolic projection line are used to form a pixels $P_{x,y}(\theta)$ in the diagnostic image in accordance with $$P_{x,y}(\theta) = \operatorname*{Max}_{z=1,N}[P_z]\bigg|_{x,y}$$

which will form a diagnostic image of the maximum intensity value along each symbolic projection line. The volume rendered image is converted to video signals by a video processor 60 and displayed on a display 100.

Figure 2:
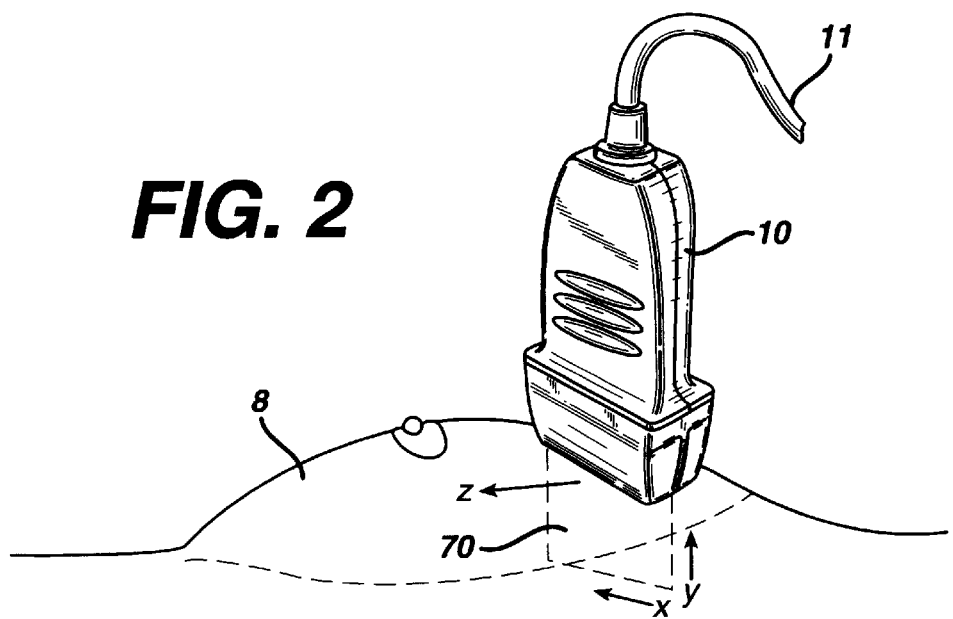
FIG. 2 illustrates ultrasonic scanning of the breast.

Methods for breast imaging in accordance with the present invention are illustrated by the following drawings. FIG. 2 illustrates the breast 8 of a reclining patient which is being scanned with a high frequency linear array scanhead 10. The scanhead shown in FIG. 2 is an L10-5 scanhead manufactured by the assignee of the present invention. The L10-5 scanhead is connected to the ultrasound system by a cable 11. The breast 8 is scanned by sliding the scanhead 10 over the surface of the breast in the direction indicated by the z arrow. To aid in sliding the scanhead and to provide good acoustic coupling, the breast surface may be coated with an acoustic couplant. A scan of the complete breast, from one extremity to the other, is preferred so that echo signals from all of the breast tissue in the z direction are acquired. As the scanhead traverses the breast it acquires a sequence of images through the breast as indicated by the scan plane outline 70, with dimensions x and y. The scanhead is held in a constant vertical orientation as shown so that the images are acquired from substantially parallel scan planes. Due to the variation in breast tissue thickness across the breast the scanhead will generally move in a slight arc in the y direction as it moves across the breast surface. The arc is minimized by the position of the patient, as the breast will flatten out somewhat when the patient is reclining. When the clinician performing the scanning is maintaining constant acoustic contact with the breast a certain amount of pressure is maintained as the scanhead moves, which will slightly compress the breast tissue beneath the scanhead.

Figure 3:
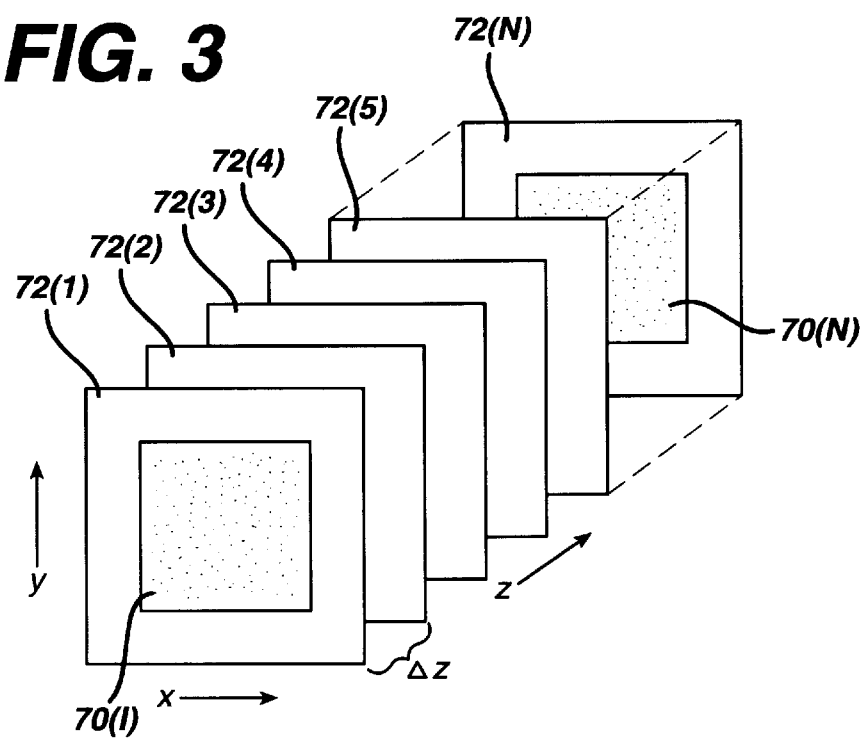
FIG. 3 illustrates an acquired set of breast images from the scanning procedure of FIG. 1.

The breast scan illustrated in FIG. 2 will produce a sequence of images 70(1)–70(N) as shown in FIG. 3. In this drawing each image in the sequence is shown on an image plane 72(1), 72(2), 72(3), 72(4), 72(5) . . . 72(N). The sequential acquisition of the images as the scanhead 10 is moved in the z direction causes each scan plane to be separated from adjacent planes by a spatial distance Δz when the scanhead is moved at a constant rate.

Figure 4:
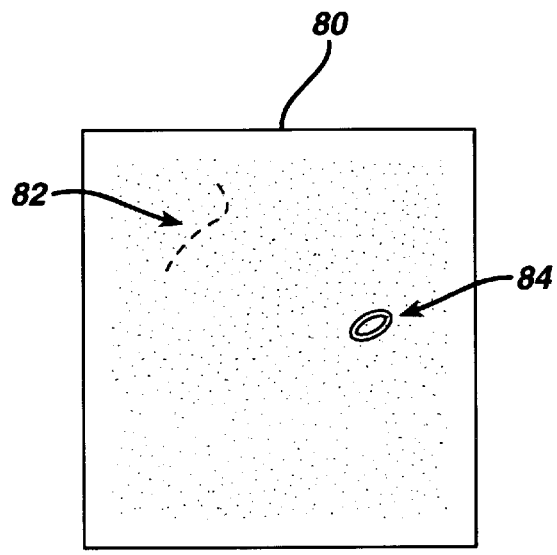
FIG. 4 illustrates a three dimensional rendering of the breast images of FIG. 3 in accordance with the principles of the present invention.

The images are then processed by volume rendering to form a composite diagnostic image 80 as shown in FIG. 4. In a preferred embodiment the rendering is performed with the images aligned on an x,y basis; that is, $P_{x,y}$ of the images are aligned for matching values of x and y. The diagnostic image 80 will exhibit characteristics of pathology of the full image set. For instance, the diagnostic image 80 includes several bright spots at 82 which appeared in one or more of the images 70(1)–70(N). (Note: for ease of illustration as a patent drawing, the image of FIG. 4 is a reversal of the black/white characteristics of an ultrasonic image.) These bright spots may be evidence of ductal microcalcifications in the breast and would thus be of interest to the diagnosing physician. The oval structure at 84 may be evidence of a cyst, which may also be of interest to the physician. These different structures 82,84 may have appeared on different images in the image sequence 70(1)–70(N), but by virtue of the volume rendering of the image data, the structures all appear on the volume rendered diagnostic image 80. Thus, the diagnosing physician can make a diagnosis of the entire breast from one or a few (if several scan sweeps are needed to cover the full breast) ultrasound images, just as can be done with mammography.

The ultrasonic imaging technique of the present invention provides an advantage not found in mammography. Like a mammogram, the image 80 will show the location of suspect pathology 82,84 in x and y coordinates, but provides no guidance as to the location of the pathology in the z dimension. However, the sequence of images from which the image 80 was formed do contain that information. The physician can identify the z coordinate of the pathology by reviewing the images of the sequence until the image is found which has the pathology in question at the x,y coordinates of the volume rendered image. The position of the image in the image sequence will identify the z coordinate of the pathology. In addition, the volume rendering can also be viewed in dynamic parallax as described in U.S. Pat. No. 5,485,842, enabling the location of the suspect pathology to be viewed in a three dimensional image display.

Figure 5:
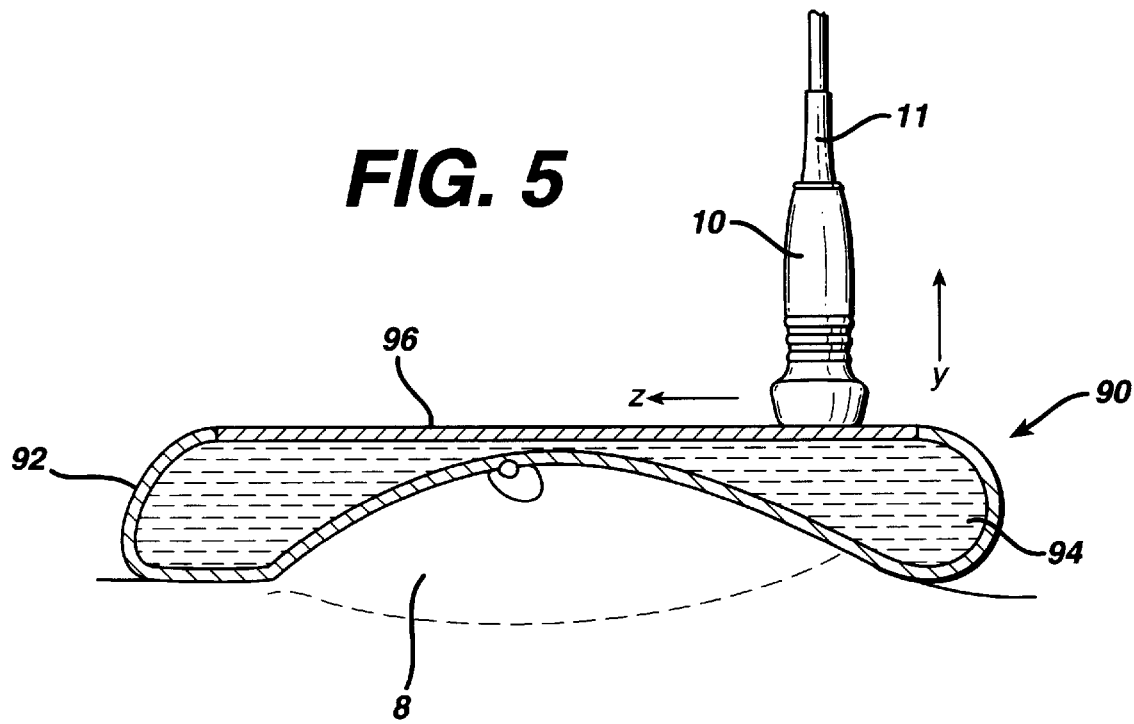
FIG. 5 illustrates a device for aiding in ultrasonic scanning of the breast.
Figure 7:
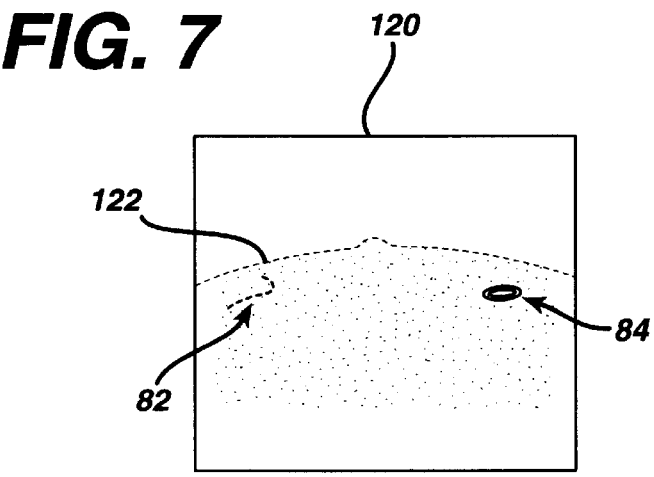
FIG. 7 illustrates a three dimensional render of breast images acquired with the aid of the devices of FIGS. 5 and 6.

FIG. 5 illustrates in cross-section a device 90 for aiding in ultrasonic scanning of the breast 8. The scanning aid 90 comprises a water bag 92 filled with water at 94 and with a semi-rigid scanning surface 96. The water bag portion of the scanning aid comprises a compliant member which conforms to the contours of the breast and provides good acoustic coupling between a scanning surface and the breast. The semi-rigid scanning surface provides a linear path across which the scanhead 10 is moved in the z direction when imaging the underlying breast 8. In use, an acoustic couplant is used to assure good acoustic coupling between the water bag 92 and the breast 8, and between the scanhead 10 and the scanning surface 96. When the scanhead 10 moves across the scanning surface 96, the flat scanning surface will provide a constant reference plane in the y dimension relative to the breast. The images acquired during the scan will retain a uniform relationship to the breast in the y dimension, and can be rendered into a diagnostic image 120, shown in FIG. 7, which retains a frame to frame spatial correspondence to the entire organ, as shown by the curvature 122 of the breast surface in the drawing. The pathological structures 82,84 which are revealed in the image will therefore exhibit a better spatial correspondence to their actual locations in the breast as compared to an image from a scan when the scanhead moved up and down while traversing the breast.

The scanning surface 96 of the scanning aid 90 is semi-rigid so as to be pliable enough to conform to the transducer window of the scanhead, a consideration when using a curved linear array for scanning. The surface 96 could itself be pre-curved in the x dimension to better conform to the convex curvature of the transducer window of a curved linear array scanhead.

Scanning of the breast in accordance with the present invention can be performed freehand with no quantification of scan plane acquisition to movement of the scanhead. In such freehand scans, the user tries to move the scanhead at a constant rate so that the image planes are separated in the z dimension by a substantially uniform separation. Through a few trials with slow scanhead movement and more rapid scanhead movement the user will arrive at a scanning speed which will produce the best images. Moving the scanhead across the breast at a slow speed will increase the sampling density of the breast in the z dimension and will produce a relatively large number of images for volume rendering. Moving the scanhead at a greater speed will decrease the sampling density in the z dimension and produce a relatively fewer number of images for volume rendering.

It may be desirable to acquire images at substantially constant spatial intervals in the z direction, which affords known and uniform sampling of the breast in that direction and provides assurance that the breast has not been undersampled and missed suspect pathology in the z direction. To do this, one must know the relative location of the scanhead in the z direction, so that each image can be acquired after passage of the required Δz distance. One way of doing this is through use of devices internal to the scanhead, such as the accelerometers described in U.S. Pat. No. 5,529,070. As taught in that patent, these internal devices respond to scanhead motion by producing signals which are resolved into positional information of the scanhead and its scan plane.

Figure 6:
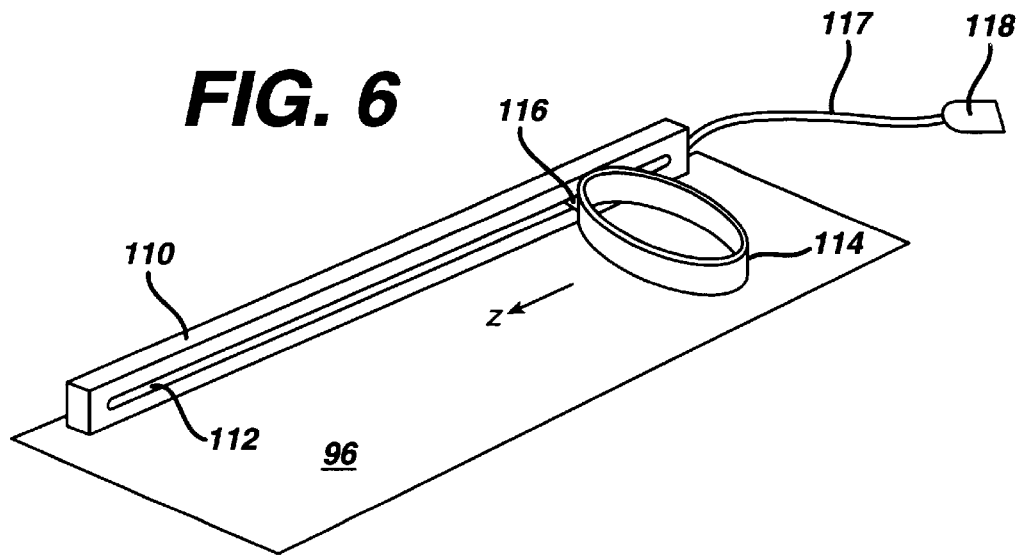
FIG. 6 illustrates a linear movement sensing device.

External devices which can be attached to the scanhead to assist in determining scanhead position during a scan may also be employed, such as that shown in FIG. 6. This drawing illustrates a linear movement sensing device 110–118 which is mounted on the scanning surface 96 of the scanning aid 90. The illustrated linear movement sensing device comprises a housing 110 which contains a linear sensor. A collar 114 is provided which engages the scanhead 10. The collar is connected to the housing 110 by a rod member 116 which engages the linear sensor in the housing 110 through an elongated aperture 112 in the side of the housing. The linear sensor in the housing 110 provides signals indicative of the position of the rod member, collar, and its engaged scanhead by means of a cable 117 which connects to the ultrasound system through a connector 118.

Figure 6A:
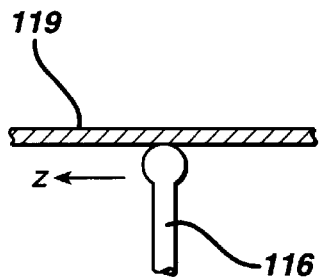
FIG. 6a illustrates a detail of the linear movement sensing device of FIG. 6.

Any of a number of types of linear sensors may be used for the linear movement sensing device. The housing 110 may contain a light source such as a series of LEDs which oppose a strip of photosensors on the other side of the housing. As the collar 114 and rod member 116 move in the z direction, the rod member 116 interrupts the light path between the LEDs and photosensors at locations along the strip. A signal indicating location of the interruption is sent to the ultrasound system to indicate the position of the scanhead. As a second alternative, a magnetic system may be employed which magnetically senses the position of a metallic rod member as it moves inside the housing. FIG. 6a illustrates an electromechanical sensor, in which the rod member 116 bears against a capacitive strip 119 as it moves in the z direction. The capacitive strip operates in the manner of a capacitive laptop computer mouse, whereby the point of surface contact is sensed and sent to the ultrasound system as a position signal.

The scanhead position signal is used by the beamformer of FIG. 1 to determine the time of acquisition of an image. For instance, the desired inter-plane spacing may be set to 0.5 mm. Each time the scanhead moves another 0.5 mm, as indicated by the position signal, the beamformer controls the scanhead 10 to acquire another image. The resultant plane sequence will be uniformly spaced by a distance of 0.5 mm. It should be remembered that absolute distance measurements are not required when the scan is started before and ends after the breast tissue, since only relative distance measurements will suffice to sample the full breast at the uniform plane spacing.

Figure 8:
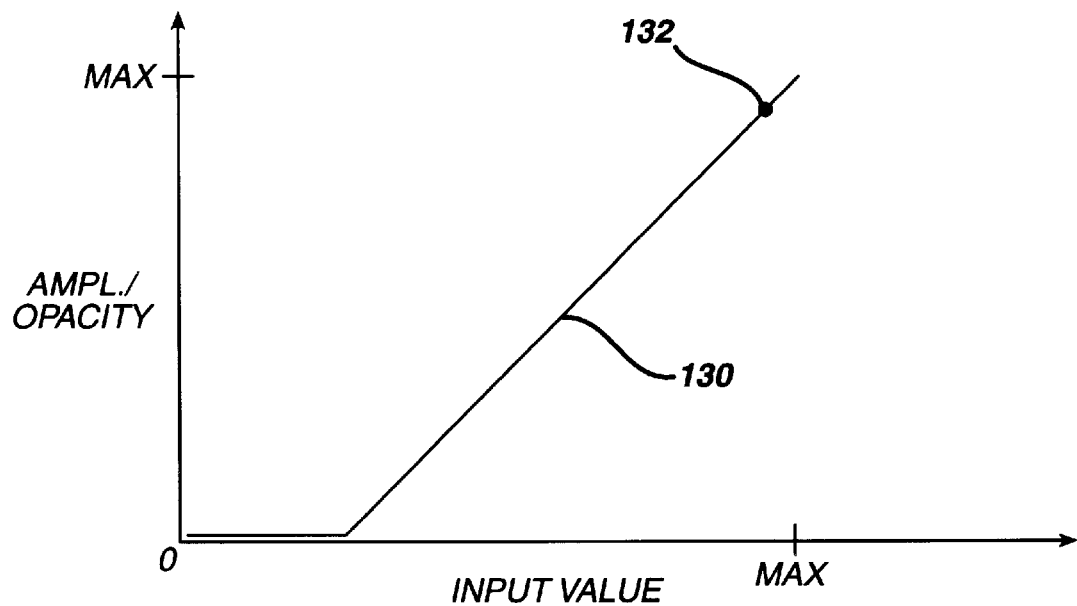
FIGS. 8 and 9 illustrate image data mapping functions for ultrasonic breast scanning in accordance with the principles of the present invention.

In accordance with another aspect of the present invention, the echo signals acquired during the breast scans can be processed to highlight only those acoustic characteristics which may indicate pathology of interest to the diagnosing physician. Microcalcifications, for instance are relatively hard calcified particles which are relatively hyperechoic, that is, they are relatively strong reflectors of ultrasonic energy. To highlight hyperechoic substances, an increasing opacity transfer characteristic 130 as shown in FIG. 8 can be used to render the volumetric image. The transfer characteristic 130 indicates the value of an output signal for a given input value along the abscissa of the drawing. The transfer characteristic 130 begins with a zero output amplitude for low level input values so that low level noise signals are suppressed. Above a certain threshold at the breakpoint of the characteristic 130, the output amplitude monotonically increases with increasing input values. This results in high level input signals, such as those received from calcifications, being produced as more opaque display pixels as indicated by point 132 on the transfer characteristic. Thus, a strong echo received from a microcalcification in the breast will be reproduced as a bright opaque dot on one or more of the images in the image sequence, and a maximum intensity volume rendering will show a bright microcalcification dot 82 in the diagnostic image 80,120. Lower level input signals from normal tissue on images in front of the microcalcification which would only obscure the pathology of interest are reproduced with a greater transparency, so that the physician will effectively see through the normal tissue and spot the suspect microcalcifications. Thus, the present invention increases lesion conspicuity by rendering lesions more opaquely than normal tissue.

The transfer characteristic 130 can be applied to the received echo signals at numerous places in the signal processing path in FIG. 1. It can be applied to B-mode echo signals in the mapping function of the detector and grayscale mapping circuit 24, or it can be applied as a mapping function during scan conversion. Preferably it is applied as a tissue rendering parameter used during volume rendering to render suspect lesions more opaque and normal tissue more transparent.

Figure 9:
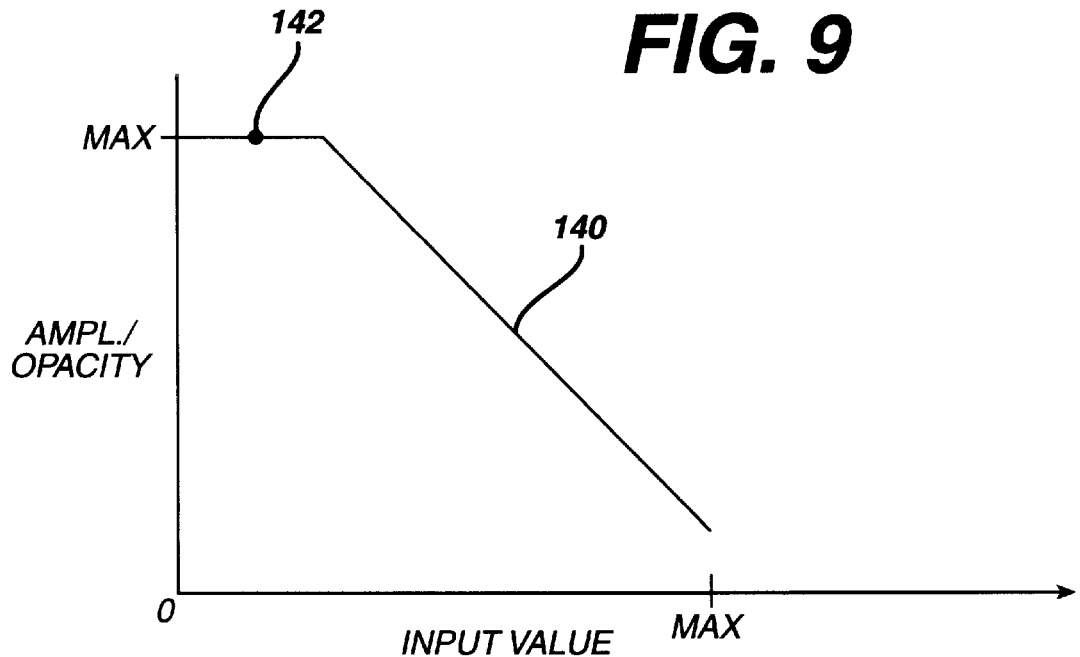

When looking for hypoechoic lesions such as a cyst 84, a decreasing opacity transfer characteristic 140 as shown in FIG. 9 may be used. A fluid filled cyst reflects relatively little acoustic energy (hypoechoic), and hence its acoustic signature is little or no echo response. A decreasing opacity transfer characteristic 140 will highlight such a response with a more opaque image pixel, since low level input values will produce a greater opacity value such as that shown by point 142 on the characteristic. This transfer characteristic will cause hypoechoic cysts 84 to be reproduced as bright opaque spots in the diagnostic image 80,120. The transfer characteristic 140 can also be applied at various points in the signal processing path, including the greyscale mapping function, scan conversion, where its effect is to produce a minimum intensity rendering for hypoechoic signal emphasis. Preferably, the characteristic is utilized as an opacity rendering parameter to render hypoechoic areas more opaque in the volume rendering.

Breast tissue contains a substantial network of small blood vessels. When highlighting hypoechoic structures in the breast as described above, the lumens of blood vessels will also be highlighted or made more opaque, due to their hypoechoic characteristic. However, unlike a cyst, a blood vessel contains a moving substance, flowing blood. Therefore, this differentiating characteristic of blood vessels can be detected and used to suppress highlighting or opaque rendering of blood vessels during breast imaging. One technique for identifying flowing blood is Doppler detection, since the movement of the blood will produce a Doppler return signal. This means that both greyscale and Doppler information can be acquired for each image, as is contained in a colorflow image. The B mode component of the colorflow image can be volume rendered to produce the diagnostic image, and the Doppler information can be used as a rendering parameter to suppress display information at locations which returned a Doppler signal. The display of lumens of blood vessels as bright or opaque areas with the transfer characteristic 140 is masked by a bloodflow rendering parameter which eliminates display information at locations which returned a Doppler signal, such as a blood vessel. The resulting diagnostic image will thus highlight or opaquely render the stationary fluid pool of a fluid filled cyst while suppressing the display of blood vessel lumens as highlighted or opaque structures through recognition of their Doppler characteristics.

The techniques of the present invention can be performed with a wide variety of ultrasonic scanheads. Mechanical scanheads which mechanically steer an ultrasonic beam to scan the breast may be employed, as well as scanheads with two dimensional array transducers which are capable of steering an ultrasonic beam to scan in three dimensions. Either of these types of scanheads may be used to acquire ultrasonic data from a volumetric region of the breast.

What is claimed is:

1. A method for producing an ultrasonic image which may contain hypoechoic tissue comprising mapping ultrasonic image data by means of a transfer function which emphasizes low level ultrasonic echo signals in relation to high level ultrasonic echo signals.

2. The method of claim 1, wherein said transfer function comprises a decreasing transfer characteristic.

3. The method of claim 1 or 2, further comprising the step of masking from display areas which return Doppler signals above a given threshold.

4. A method for imaging hypoechoic structures of the breast comprising the steps of:

processing ultrasonic echo information received from a region of the breast to produce B mode signals;

processing ultrasonic echo information received from said region of the breast to produce Doppler signals;

processing said B mode signals to produce image signals which emphasize hypoechoic areas of said region; and suppressing the display of hypoechoic areas of said region which correspond to said Doppler signals.

5. A method for producing diagnostic ultrasonic images of a breast, comprising the steps of:

acquiring an ultrasonic data set of a volumetric region of a breast; and volume rendering said ultrasonic data to produce a projection image of said data of said volumetric region, wherein said volume rendering comprises utilizing an opacity transfer function which renders lesions with greater opacity than normal tissue.

6. The method of claim 5, wherein said opacity rendering parameter exhibits an increasing transfer characteristic.

7. The method of claim 6, wherein said opacity rendering parameter renders calcified substances in the breast with greater opacity than normal tissue.

8. The method of claim 5, wherein said opacity rendering parameter exhibits a decreasing transfer characteristic.

9. The method of claim 8, wherein said opacity rendering parameter renders hypoechoic regions in the breast with greater opacity than normal tissue.

10. The method of claim 9, further comprising the step of suppressing the rendering of blood vessel lumens as opaque regions.

* * * * *